United States Patent [19]

Baldi et al.

[11] 4,224,444

[45] Sep. 23, 1980

[54] PROCESS FOR THE PREPARATION OF CHLORO-BIS(ALKYLAMINO)-S-TRIAZINES

[75] Inventors: Luciano Baldi; Vittorio Messori; Renato Francese, all of Turin, Italy

[73] Assignee: Rumianca S.p.A., Turin, Italy

[21] Appl. No.: 80,721

[22] Filed: Oct. 1, 1979

[51] Int. Cl.³ ............................................. C07D 251/50
[52] U.S. Cl. ..................................................... 544/204
[58] Field of Search .......................................... 544/204

[56] References Cited

U.S. PATENT DOCUMENTS

| | | | |
|---|---|---|---|
| 3,436,394 | 4/1969 | Saul | 544/204 |
| 3,590,040 | 6/1971 | Ferguson et al. | 544/204 |
| 3,639,399 | 2/1972 | Daugherty et al. | 544/204 |
| 3,681,335 | 8/1972 | Saul et al. | 544/204 |
| 3,681,337 | 8/1972 | Petree | 544/204 |
| 4,054,739 | 10/1977 | Haschke et al. | 544/204 |
| 4,058,662 | 10/1977 | Haschke et al. | 544/204 |
| 4,099,006 | 7/1978 | Baldi et al. | 544/204 |

*Primary Examiner*—John M. Ford
*Attorney, Agent, or Firm*—Sughrue, Rothwell, Mion, Zinn and Macpeak

[57] ABSTRACT

Chloro-bis(alkylamino)-s-triazine is prepared by means of the step-wise replacement of two chlorine atoms of cyanuric chloride with alkylamino groups in an alkaline medium comprising water and a liquid organic compound which is a solvent for cyanuric chloride and forms a two-phase system with water, in which a molar excess of alkylamine is used in the second replacement step. Upon completion of the second replacement step the reaction mixture is freed from its aqueous phase and the residual suspension or solution of triazine in the organic compound is admixed with water added in a volumetric quantity of from 30 to 150% with respect to that of said aqueous phase.

The chloro-bis(alkylamino)-s-triazine thus produced has high characteristics of handling and formulability.

12 Claims, No Drawings

PROCESS FOR THE PREPARATION OF CHLORO-BIS(ALKYLAMINO)-S-TRIAZINES

The present invention relates to an improved procedure for the preparation of chloro-bis (alkylamino)-s-triazines having high characteristics of handling and formulability.

The chloro-bis (alkylamino)-s-triazines are compounds definable by means of the general formula:

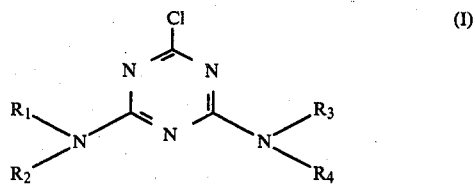

where $R_1$, $R_2$, $R_3$ and $R_4$ independently are hydrogen, an alkyl radical containing from 1 to 5 atoms of carbon, or particular groups of a different nature from the alkyl group.

The chloro-bis (alkylamino)-s-triazines are valued herbicides and the compounds most known belonging to this group are: 2-chloro-4-ethylamino-6-isopropylamino-s-triazine (atrazine), 2-chloro-4, 6-bis(ethylamino)-s-triazine (simazine) and 2-chloro-4, 6-bis (isopropylamino)-s-triazine (propazine). The herbicidal characteristics of these compounds are described in U.S. Pat. No. 2,891,855 here given as a reference.

The chloro-bis (alkylamino)-s-triazines are generally prepared from cyanuric chloride by step-wise replacement of two atoms of chlorine, as reported, for example, by W. Pearlman and C. K. Banks in J. Am. Chem. Soc. 70, 3726 (1948). In practice the reaction is carried out according to the general scheme:

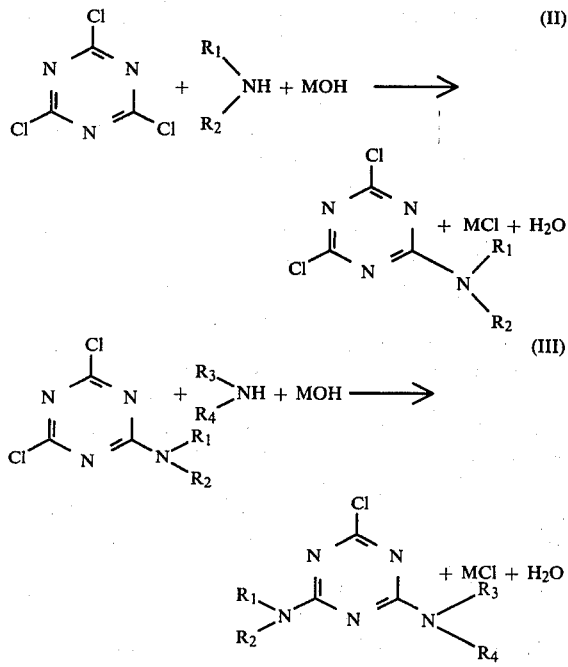

where M represents an alkali metal.

In particular the preparation of atrazine is generally carried out by a discontinuous method, by reacting, in a first reaction stage, cyanuric chloride with isopropylamine in the presence of sodium hydroxide to give 2,4-dichloro-6-isopropylamino-s-triazine. This latter is reacted, in a second stage, with ethylamine and with a further quantity of sodium hydroxide with the subsequent formation of the desired product: 2-chloro-4-ethylamino-6-isopropylamino-s-triazine.

The reactions described may be carried out in an aqueous medium or in an organic medium. Generally it is preferred to conduct the reactions in a water-organic compound medium, using as the organic compound a solvent for cyanuric chloride which is insoluble in water, or is partially or totally soluble in the same, i.e., two-phase or single-phase water-organic compound systems.

Generally the reaction (II) given above is carried out by using stoichiometric quantities of the reagents, while the reaction (III) is carried out with a quantity of alkylamine and of sodium hydroxide greater than those needed for the production of chloro-bis (alkylamino)-s-triazine. This method of operation is justified by the need to completely convert the 2,4-dichloro-6-alkylamino-s-triazine in view of the undesirable characteristics of such a compound. Thus, for example, 2,4-dichloro-6-isopropylamino-s-triazine has skin-irritant properties to such an extent that it must not be present in the final product in quantities greater than about 0.5% by weight.

On the other hand the use of excess alkylamine results in disadvantages due for example to the formation of tris (alkylamino)s-triazine by reaction of the excess alkylamine with the chloro-bis (alkylamino)-s-triazine. For example, the reaction of ethylamine with 2-chloro-4-ethylamino-6-isopropylamino-s-triazine results in the formation of 2,4-bis (ethylamino)-6-isopropylamino-s-triazine. This latter compound is undesirable in that it renders the recovery of atrazine from the reaction products difficult, hinders the grinding of the dried atrazine and reduces the stability and flowability of the liquid formations containing atrazine. Probably these undesirable effects are caused, at least in part, by the 2,4-bis (ethylamino)-6-isopropylamino-s-triazine, which is a tacky solid of low melting point and waxy appearance. This by-product mainly forms in the stage of recovery of the reaction products, especially in the stage of distillation of the organic solvent used in the reaction medium, rather than during the reaction (III) described above.

Therefore various expedients have been proposed in the art to deactivate the unreacted alkylamine at the end of the reaction (III).

Thus, for example, according to U.S. Pat. No. 3,681,335 on completion of the formation of the chloro-bis (alkylamino)-s-triazine, a strong acid is added to the reaction medium to bring the pH from 11.5–12 to values of the order of 5–9 (preferably of the order of 6.5–7.5). In this manner the alkylamine is deactivated and the distillation of the organic solvent may be carried out without danger of formation of tris (alkylamino)-s-triazine. According to the patent under discussion, the pH is brought back to values of the order of 11-12.5 in the residual suspension from the distillation containing the chloro-bis (alkylamino)-s-triazine before the separation of the latter is carried out by means of filtration. The characteristics of filterability are thus improved.

Moreover, according to U.S. Pat. No. 3,681,337, immediately after the end of reaction (III), cyanuric chloride is added to the reaction mixture in such amounts as to neutralize the free amine and from the dichloro-alkylamino-s-triazine, which is then hydrolyzed together with the free cyanuric chloride. Since the hydrolysis products are soluble in water their removal becomes easy.

Finally, according to U.S. Pat. No. 3,705,156 formaldehyde is added to the products of the reaction (III), in order to induce the formation of condensation products between formaldehyde and the free alkylamine. These condensation products are removed during the distillation and the subsequent filtration.

These known processes while only achieving the object of minimising the formation of the tris (alkylamino)-s-triazine, have disadvantages due to the addition of further substances to the reaction medium with consequent formation of new chemical species which must be removed from the reaction product.

Such a method of operation may lead to a worsening on the purity of the desired product, and is moreover burdensome due to the number and type of treatments required.

An object of the present invention is to prepare chloro-bis (alkylamino)-s-triazines having good handling and characteristics, while avoiding the above disadvantages.

The invention provides a process for preparing chloro-bis (alkylamino)-s-triazine by means of the step-wise replacement of two chlorine atoms of cyanuric chloride with alkylamino groups in an alkaline medium comprising water and a liquid organic compound which is a solvent for cyanuric chloride and forms a two-phase system with water, in which a molar excess of alkylamine is used in the second replacement step and in which said organic compound is removed by distillation from the reaction mixture resulting from the second replacement step, characterized in that upon completion of the second replacement step said reaction mixture is freed from its aqueous phase and the residual suspension or solution of chloro-bis (alkylamino)-s-triazine in the organic compound thus obtained is admixed, prior to or during the distillation of the organic compound, with water added in a volumetric quantity of from 30 to 150% with respect to that of said aqueous phase.

The present invention is essentially based on the finding that, when the step-wise replacement is carried out in a two-phase water-organic compound medium, chloro-bis (alkylamino)-s-triazines with a high degree of purity and excellent characteristics of handling and formulability can be obtained by freeing the reaction mixture resulting from the step-wise reaction from the aqueous phase, and adding water to the residual organic phase thus obtained, prior to, and/or during the removal of the organic compound by distillation. At the end of the reaction (III) the chloro-bis (alkylamino)-s-triazine may be dissolved in the organic phase or suspended partially or totally in the reaction mixture depending on the range of conditions in which the reaction (III) is carried out. In either case according to the present invention, the aqueous phase is first removed and then the organic solvent is reintegrated with water before and/or during the distillation.

At the end of the distillation, an aqueous suspension of the chloro-bis (alkylamino)-s-triazine is obtained as a distillation residue from which this latter product is separated free from tris (alkylamino)-s-triazine, or at least with a content of this latter less than 0.05% by weight.

The process of the present invention has also the advantage that the aqueous suspension of the chloro-bis (alkylamino)-s-triazine which is obtained after the distillation of the organic solvent contains only traces of the usual polluting substances, such as substances resulting from the possible hydrolysis of the cyanuric chloride and the alkali metal chloride formed in the course of the reaction, which must be removed in the conventional processes by washing treatments of the chloro-bis (alkylamino)-s-triazine.

According to the desired use of the final product, the suspension may be treated by one of the following methods:

(a) when it is desired to obtain the chloro-bis (alkylamino)-s-triazine as a technical product, the suspension is filtered or centrifuged without any subsequent washing.

One then proceeds to the drying which may be carried out by the spray technique;

(b) when it is desired to obtain the chloro-bis (alkylamino)-s-triazine directly as a concentrated suspension, the water added either before or during the distillation of the organic solvent is measured so as to produce a suspension having the desired concentration of solids, which is admixed with formulation additives and then submitted to milling under wet conditions. For the purpose of improving the characteristics of fluidity it is possible to add suitable dispersing agents, such as for example lignin sulphonates, this addition being effected before, during or after the distillation of the organic solvents;

(c) when it is desired to obtain the chloro-bis (alkylamino)-s-triazine directly in the form of wettable powders, it suffices to add to the suspension the conventional formulation additives, and to carry out then a wet milling and a drying, for example a spray drying.

The chloro-bis (alkylamino)-s-triazines obtained according to the present invention are useful in herbicidal formulations (both as wettable powders and as liquid suspensions) which are characterized by a great facility of use and by an increased herbicidal efficiency. These formulations do not have any of those known disadvantages resulting from the presence of tris (alkylamino)-s-triazines in their storage or their use.

By means of the process of the present invention there may be prepared all the compounds definable by means of the general formula (I), in which $R_1$, $R_2$, $R_3$ and $R_4$ independently are hydrogen, alkyl radicals either the same or different, having from 1 to 5 atoms of carbon, or other particular groups different from alkyl groups. Examples of alkyl radicals are: methyl, ethyl, isopropyl, cyclopropyl, n-butyl, sec-butyl and tert-butyl. The alkylamino groups are preferably monoalkylamino groups.

In the description which follows, specific reference will be made to the preparation of 2-chloro-4-ethylamino-6-isopropylamino-s-triazine. This is for reasons of simplicity, it being taken into account that wholly similar considerations are valid for the other chloro-bis (alkylamino)-s-triazines.

(a) Preparation of 2,4-dichloro-6-isopropylamino-s-triazine

In stage (a) cyanuric chloride, isopropylamine and sodium hydroxide are reacted to produce 2,4-dichloro-6-isopropylamino-s-triazine according to the following scheme:

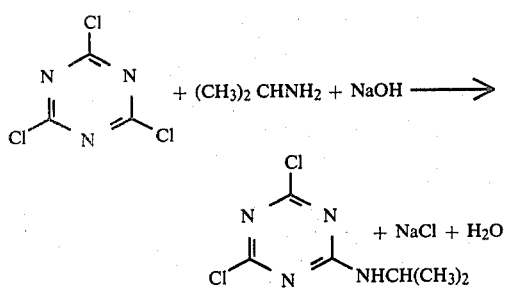

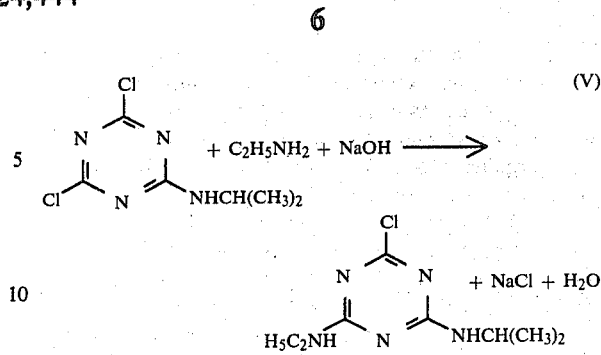

The quantities of isopropylamine and of sodium hydroxide are equivalent, or nearly equivalent, to those needed for the formation of the 2,4-dichloro-6-isopropylamino-s-triazine. In place of sodium hydroxide there may be used sodium carbonate, or the hydroxide or carbonate of other alkali metals, such as lithium and potassium.

The reaction is carried out in the presence of water and an organic compound substantially immiscible with water, inert under the reaction conditions and having a good solvating power towards cyanuric chloride. Organic solvents suitable for the purpose are for example diethyl ether, benzene, toluene, xylene, chlorobenzene, methyl ethyl ketone and carbon tetrachloride. The preferred two-phase systems are water-toluene and water-chlorobenzene.

As a rule the cynauric chloride is fed in the form of a solution in the chosen organic solvent, while the inorganic base and the alkylamine are fed in the form of an aqueous solution. In the choise of the solvent it is also necessary to take account of its separability, by means of distillation, from the chloro-bis (alkylamino)-s-triazine finally produced. The quantities of organic solvent and of water used are not particularly critical; it is however, convenient to maintain the weight ratios between the two at values of from 3:1 to 3:2. Moreover good results are obtained by regulating the feeds such that the concentration of the 2,4-dichloro-6-isopropylamino-s-triazine at the end of stage (a) is from 10 to 20% by weight with respect to the weight of the chosen organic solvent.

The temperature is generally kept at a value of from $-5°$ to 60° C. Overpressure is not generally applied, or the overpressure necessary to maintain the reaction medium in the liquid phase is applied.

The 2,4-dichloro-6-isopropylamino-s-triazine may be prepared by using a continuous or a discontinuous process. In the second case the sodium hydroxide and the isopropylamine are generally added in the form of aqueous solutions to the cyanuric chloride dissolved in the chosen organic solvent.

At the end of stage (a) it is possible to carry out a separation of materials from the reaction mixture, such as the aqueous phase, but generally the reaction mixture is conveyed directly to the following reaction stage.

(b) Preparation of 2-chloro-4-ethylamino-6-isopropylamino-s-triazine

In stage (b) the 2,4-dichloro-6-isopropylamino-s-triazine obtained in stage (a), ethylamine and sodium hydroxide, are reacted to produce 2-chloro-4-ethylamino-6-isopropylamino-s-triazine according to the scheme:

The ethylamine and sodium hydroxide are generally used in a molar recess of from 1% to 6%. Usually this excess is maintained at values of the order of 3%. The ethylamine and the sodium hydroxide are conveniently fed in in the form of an aqueous solution.

The reaction is conveniently carried out at a temperature of from $-5°$ to $+80°$ C. and for a period such as to completely convert the 2,4-dichloro-6-isopropylamino-s-triazine, or at least to convert more than 99.5% of this compound. The other operating conditions for stage (b) are entirely similar to those described for stage (a).

The above conditions are particularly suitable when using a semi-continuous process, in particular for the preparation of atrazine, in which the amine and the sodium hydroxide are fed to a liquid medium containing the cyanuric chloride dissolved in the pre-chosen organic solvent. In such a case, at the end of stage (b) a suspension of the atrazine is generally obtained and this suspension is subjected to the aforesaid treatments.

It is possible to obtain a reaction product in which the atrazine is completely dissolved in the liquid phase by carrying out the reaction with short contact times and at relatively high temperatures. In particular these conditions occur when the step-wise replacement is carried out by a continuous process, operating under turbulent conditions and in total times less than about ten minutes, and using a temperature of up to about 90° C. in the first substitution and up to 100° C. in the second substitution of the chlorine atoms in the cyanuric chloride. By operating under these conditions, it is possible to obtain a reaction product consisting of an aqueous phase and an organic phase, this latter containing the atrazine in a dissolved form. Moreover according to a particular aspect of this method, the substitution of the second atom of chlorine of the cyanuric chloride may be carried out within a range of temperature less than those corresponding to the solubility of the reaction product in the reaction medium, but in the absence of precipitation, above all in view of the brief reaction times used. In this case, also, a reaction product is separated in which the atrazine is dissolved in the liquid phase even though the conditions are those of super-saturation.

Elimination of the aqueous phase and separation of the reaction product (stage c)

The suspension or solution of the atrazine in the two-phase medium obtained from the preceeding stage (b) is first freed from the aqueous phase. This separation may be carried out at a temperature of from 20° to 100° C. Obviously the upper temperatures are used in cases in which the atrazine is in solution for the purpose of maintaining this physical state. It is also noted that supersaturated solutions obtained by means of the aforesaid continuous process, are maintained in this state for sufficiently long periods of time to allow easy separation of the aqueous phase, as long as substantial lowerings of temperature with respect to that at the outlet from stage (b) do not occur in this separation. The separation of the aqueous phase may also be carried out continuously. The organic phase thus obtained is combined with water added in volumetric quantities of from 30% to 150% with respect to the aqueous phase discharged, and preferably in a quantity of the same order of magnitude as this aqueous phase. According to a preferred embodiment, the water is fed gradually to the organic phase during the distillation of the organic solvent. The distillation may be carried out at a pressure equal to, or less than, atmospheric and the distillation residue consists, in every case, of an aqueous suspension of atrazine. This suspension may be filtered and dried, or conveyed directly to a spray drier, or directly made into formulations as a concentrated liquid suspension or as a wettable powder. In every case the bis (alkylamino)-s-triazine thus obtained contains less than about 0.05% by weight of tris (alkylamino)-s-triazine.

EXAMPLE 1

A reactor of 20 liter capacity, provided with an agitator, a thermometer and two separate apertures for the feed of the reagents, is used. The reactor is furnished with means for its cooling. Into the reactor is loaded initially a solution of about 1840 g (10 moles) of cyanuric chloride in about 5000 g of toluene (boiling point 110.6° C.). Hardly has the temperature of the solution stabilized at 5° C. than there are simultaneously added, under strong agitation, 840 g of an aqueous solution containing 70% by weight of isopropylamine (10 moles) and 1340 g of an aqueous solution containing 30% by weight of sodium hydroxide (10 moles). The two feed rates are controlled so that the addition of the isopropylamine solution finishes in 25 minutes and that of the sodium hydroxide in 28 minutes.

During the addition, the temperature rises from 5° C. up to 20°–22° C., while the pH, from an initial value of 2–3, rises to a maximum value of 9.5 then to fall to 6–7.

After the addition, there are added to the mixture under strong agitation, about 915 g of an aqueous solution containing 50% by weight of ethylamine (10.15 moles) and about 1353 g of an aqueous solution containing 30% by weight of sodium hydroxide (10.15 moles). The said solutions are added in the same manner as in the first reaction step. During the second addition the temperature rises from 25° to 50° C. and the final pH value is equal to 12.5. The dense suspension thus obtained is divided into two parts as quickly as possible. One part (A) is submitted to distillation to remove the toluene in the form of an azeotropic toluene-water mixture, by operating at 85°–100° C. To the distillation residue are added 1,500 ml of water and the suspension thus obtained is filtered at 60° C. The filtered solid is washed until the sodium chloride has been removed completely. After drying for ten hours in an oven at 100° C., 2-chloro-4-ethylamino-6-isopropylamino-s-triazine is obtained with a yield of the order of 96% and a purity of about 98%.

The other part (B) is freed from the aqueous phase and the latter is replaced by an equal volume of water.

The sample (B) is then submitted to the treatments of distillation and recovery of atrazine from the distillation residue, by operating under the same conditions as in the case of sample (A) but omitting the washing step.

The product obtained from sample (B) consists of atrazine with a yield of about 96% and a purity of about 98%.

Suspensions are prepared from the products obtained from samples (A) and (B) with a concentration of 45% by dispersing the finely ground atrazine in a liquid medium consisting of water, wetting agents, dispersing agents and suspending agents. The fluidity of the formulate is determined immediately after the formulation and after three month and six months of storage under ambient conditions. The results are summarized in Table I.

EXAMPLES 2 and 3

Two runs are carried out as in Example 1 using respectively 3% and 6% molar excess of ethylamine with respect to the stoichiometric value.

The results are summarized in Table I. The content of 2,4-bis (ethylamino)-6-isopropylamino-s-triazine in the products obtained from the samples (B) is in every case less than the quantity which can be determined analytically.

TABLE I

| Example | Sample | % Molar Excess of EtNH$_2$ | Initial | Fluidity After 3 Months | After 6 Months |
|---------|--------|----------------------------|---------|-------------------------|----------------|
| 1 | A | 1.5 | fluid | thick | — |
| 1 | B | 1.5 | fluid | fluid | fluid |
| 2 | A | 3.0 | fluid | thick | — |
| 2 | B | 3.0 | fluid | fluid | fluid |
| 3 | A | 6.0 | fluid | thick | — |
| 3 | B | 6.0 | fluid | fluid | fluid |
| 4 | C$_1$ | 3.0 | fluid | fluid | fluid |
| 4 | C$_2$ | 3.0 | fluid | thick | — |

EXAMPLE 4

A reactor consisting of a stainless steel tube having a length of ten meters, an internal diameter of 4 mm and an external diameter of 6 mm is used. The tube is filled with grains of sand having a size of 1.2 to 1.8 mm, with a bulk density of 1.48 g/cm$^3$ and with a specific gravity of 2.6 g/cm$^3$. The first 2.5 meters are used for the formation of the 2,4-dichloro-6-alkylamino-s-triazine (stage a) and the remaining part is intended for the production of the 2-chloro-4-ethylamino-6-isopropylamine-s-triazine (stage b). More particularly, to the inlet to stage (a) are fed 43 ml/min of a toluene solution containing 15% by weight of cyanuric chloride and independently 13.8 ml/min of an aqueous solution containing 12.77% by weight of isopropylamine and 8.85% by weight of sodium hydroxide. Thus the molar ratio between cyanuric chloride, isopropylamine and sodium hydroxide at the inlet to stage (a) is equal to 1:1:1.

The reaction of stage (a) is carried out adiabatically with an inlet temperature of 18° C. and an outlet temperature of 55° C.

No heat-exchange is effected between the two reaction stages and to the inlet to stage (b) are fed 11.4 ml/min of an aqueous solution containing 12.15% by weight of ethylamine (3% molar excess with respect to the stoichiometric value) and 11.25% by weight of sodium hydroxide. This solution is fed in at a temperature of 18° C. The reaction of stage (b) is also carried out adiabatically and the temperature of the mass at the outlet end of the reactor is 70° C. The mixture discharged from the reactor is conveyed to a phase separator heated to 70° C., operating continuously, where the aqueous phase is separated from the toluene phase containing the atrazine.

This toluene phase is then continuously fed to a distillation unit into which water is also fed at a rate of 25 ml/min. The aqueous atrazine suspension recovered as a distillation residue is admixed with conventional formulation additives and is then submitted to a milling under wet conditions (sample $C_1$). For the purpose of a control, the reaction mixture discharged from the tubular reactor is conveyed directly to the distillation unit and the aqueous atrazine suspension obtained as a distillation residue is subjected to the conventional washing, admixed with the formulation additives and then submitted to the milling under wet conditions (sample $C_2$). The characteristics of fluidity of the two samples under storage at ambient temperature are shown in Table I.

We claim:

1. In a process for preparing chloro-bis (alkylamino)-s-triazine of high characteristics of handling and formulability by means of the step-wise replacement of two chlorine atoms of cyanuric chloride with alkylamino groups in an alkaline medium comprising water and a liquid organic compound which is a solvent for cyanuric chloride and forms a two-phase system with water, in which a molar excess of alkylamine is used in the second replacement step and in which said organic compound is removed by distillation from the reaction mixture resulting from the second replacement step, the improvement which comprises feeding, upon completion of the second replacement step, said reaction mixture from its aqueous phase and admixing the residual suspension or solution of chloro-bis (alkylamino)-s-triazine in the organic compound thus obtained, prior to, or during the distillation of the organic compound, with water added in a volumetric quantity of from 30 to 150% with respect to that of said aqueous phase.

2. The process of claim 1, wherein said organic compound is selected from the group consisting of diethyl ether, benzene, toluene, xylene, chlorobenzene, methyl ethyl ketone and carbon tetrachloride.

3. The process of claim 1 wherein said organic compound is toluene.

4. The process of claim 1, wherein the weight ratio between said organic compound and said water is from 3:1 to 3:2.

5. The process of claim 1, wherein said molar excess of alkylamine is from 1 to 6%.

6. The process of claim 1, wherein said aqueous phase is removed at a temperature of from 20° to 100° C.

7. The process of claim 1, wherein the volumetric quantity of said added water is substantially equivalent to that of said aqueous phase.

8. The process of claim 1, wherein said added water is gradually admixed with said suspension or solution during said distillation.

9. The process of claim 1, wherein the amount of added water is measured so as to obtain as a residue of said distillation an aqueous suspension of chloro-bis (alkylamino)-s-triazine directly utilizable for the preparation of liquid formulates and wettable powders.

10. The process of claim 1, wherein the chloro-bis (alkylamino)-s-triazine is separated from the aqueous suspension obtained as a residue of said distillation, and directly dried without any preliminary washing.

11. The process of claim 1, wherein a chloro-bis (alkylamino)-s-triazine is produced with a content of tris (alkylamino)-s-triazine of less than 0.05% by weight.

12. The process of claim 1, wherein 2-chloro-4-ethylamino-6-isopropylamino-s-triazine is produced with a content of 2,4-bis (ethylamino)-6-isopropylamino-s-triazine of less than 0.05% by weight.

* * * * *